(12) United States Patent
Duquette et al.

(10) Patent No.: US 8,100,125 B2
(45) Date of Patent: Jan. 24, 2012

(54) VENTURI GEOMETRY DESIGN FOR FLOW-GENERATOR PATIENT CIRCUIT

(75) Inventors: Steven Duquette, Laguna Niguel, CA (US); Alex Stenzler, Long Beach, CA (US); Steve Han, Upland, CA (US)

(73) Assignee: CareFusion 207, Inc., San Diego, CA (US)

( * ) Notice: Subject to any disclaimer, the term of this patent is extended or adjusted under 35 U.S.C. 154(b) by 1094 days.

(21) Appl. No.: 11/241,303

(22) Filed: Sep. 30, 2005

(65) Prior Publication Data

US 2007/0074724 A1    Apr. 5, 2007

(51) Int. Cl.
*A61M 11/00* (2006.01)

(52) U.S. Cl. .................. 128/204.25; 128/204.18

(58) Field of Classification Search ............ 128/204.25, 128/200.24, 204.18, 203.22, 200.21, 200.23, 128/207.18

See application file for complete search history.

(56) References Cited

U.S. PATENT DOCUMENTS

| | | | |
|---|---|---|---|
| 2,985,357 A | 5/1961 | Carolan | |
| 3,319,627 A * | 5/1967 | Windsor | 128/204.25 |
| 3,630,196 A | 12/1971 | Bird | |
| 3,853,105 A * | 12/1974 | Kenagy | 128/204.25 |
| 3,881,480 A * | 5/1975 | Lafourcade | 128/200.21 |
| 3,993,081 A | 11/1976 | Cussell | |
| 4,018,221 A | 4/1977 | Rennie | |
| 4,098,290 A | 7/1978 | Glenn | |
| 4,261,355 A | 4/1981 | Glazener | |
| 4,282,869 A | 8/1981 | Zisulka | |
| 4,417,573 A * | 11/1983 | De Vries | 128/204.25 |
| 4,495,946 A | 1/1985 | Lemer | |
| 4,537,188 A | 8/1985 | Phuc | |
| 4,681,100 A | 7/1987 | Brychta et al. | |
| 4,782,832 A * | 11/1988 | Trimble et al. | 128/207.18 |
| 4,796,617 A | 1/1989 | Matthews et al. | |
| 4,915,105 A | 4/1990 | Lee | |
| 4,919,128 A | 4/1990 | Kopala et al. | |
| 5,000,173 A | 3/1991 | Zalkin et al. | |
| 5,113,857 A | 5/1992 | Dickerman et al. | |
| 5,193,532 A * | 3/1993 | Moa et al. | 128/204.25 |
| 5,259,376 A | 11/1993 | Bales | |
| 5,271,391 A * | 12/1993 | Graves | 128/207.18 |
| 5,477,852 A | 12/1995 | Landis et al. | |
| 5,752,510 A | 5/1998 | Goldstein | |
| 5,865,174 A | 2/1999 | Kloeppel | |
| 6,260,549 B1 * | 7/2001 | Sosiak | 128/200.23 |
| 6,431,172 B1 | 8/2002 | Bordewick | |
| 2003/0200970 A1 | 10/2003 | Stenzler | |
| 2005/0011524 A1 * | 1/2005 | Thomlinson et al. | 128/207.18 |

FOREIGN PATENT DOCUMENTS

| | | |
|---|---|---|
| DE | 3119814 | 12/1982 |
| WO | WO 94/06497 | * 3/1994 |

* cited by examiner

*Primary Examiner* — Steven Douglas

(57) ABSTRACT

Provided is a universal interface adapted for providing continuous positive airway pressure to a patient when the interface is used with a standard ventilator. The interface is configured to operate at a supply pressure no greater than about 120 centimeters of $H_2O$ in order to deliver pressure to the patient of up to about 15 cm of $H_2O$ at a flow rate of up to about 12 liters/minute. The universal interface may comprise an interface body having a space pair of breathing passageways intersecting a corresponding of supply passageways. Each one of the breathing passageways is comprised of a patient passageway and an exhalation passageway. Each one of the supply passageways includes a jet venturi having a taper portion. Each one of the exhalation passageways includes a taper portion which tapers outwardly along a direction from the patient passageway toward the exhalation passageway.

14 Claims, 4 Drawing Sheets

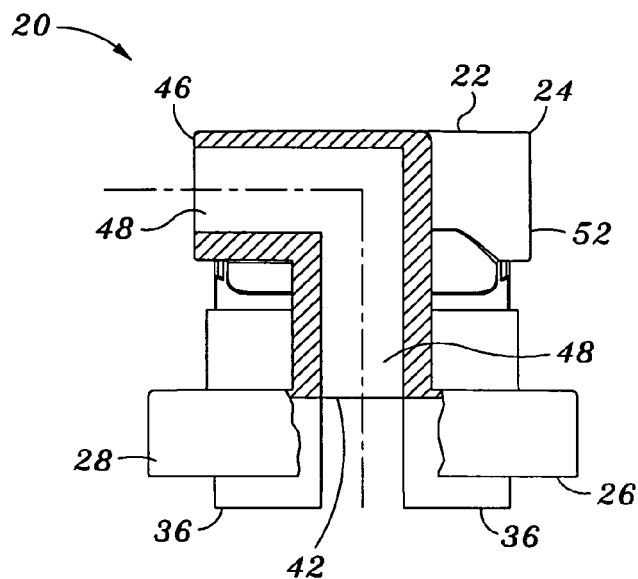
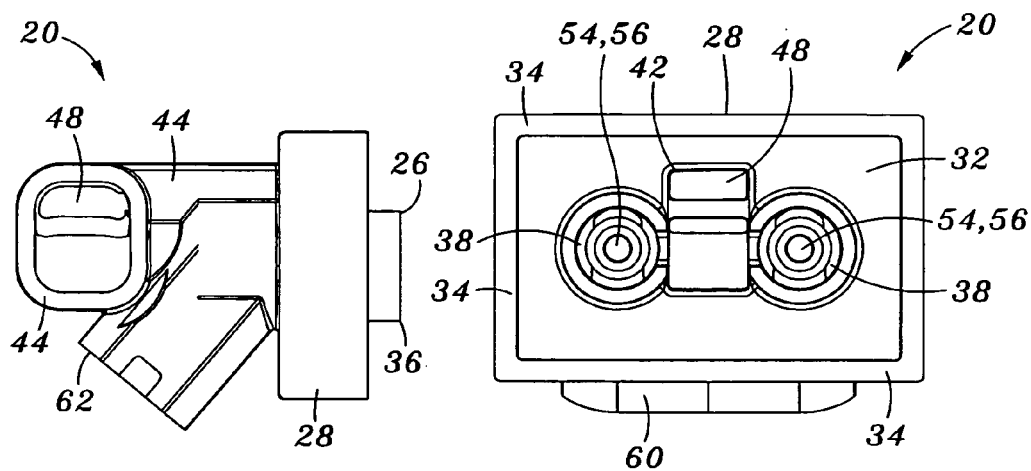

VENTURI GEOMETRY DESIGN FOR FLOW-GENERATOR PATIENT CIRCUIT

FIELD OF THE INVENTION

The present invention relates generally to a breathing apparatus.

BACKGROUND OF THE INVENTION

The present invention relates generally to breathing apparatus and, more particularly, to a universal interface for a breathing apparatus which is specifically adapted to provide continuous positive airway pressure (CPAP) when the interface is used with a standard ventilator and which further is constructed with unique geometries to increase stagnation pressure (i.e., patient pressure) with minimal supply pressure as well as reduced exhalation resistance in order to improve the work of breathing.

The use of breathing apparatus upon respiratory-impaired patients is well known. Generally, such apparatuses assist in patient breathing by allowing proper exchange of inhaled and exhaled gas while providing pressurized gasses to a patient's lungs so as to prevent lung collapse. In this manner, conventional breathing apparatus operate to allow spontaneous breathing of the patient while sustaining the application of continuous positive airway pressure (CPAP) to the patient's lungs.

The types of breathing apparatus mentioned above have proven to be effective in patients whose ability to breathe is impaired. For example, babies born with lung disease or other complications may require ventilatory support using CPAP therapy. Ideally, CPAP therapy delivers a constant stable pressure to the mouth, nose or via a tracheal tube inserted in the infant. Although the use of such apparatus has generally proven to be suitable for their intended purposes, such prior art breathing apparatus possess certain design deficiencies which detract from their overall effectiveness and desirability.

For example, flow generators are a type of device that can be used with the above-mentioned breathing apparatus in providing CPAP therapy treatment. As was earlier mentioned, in CPAP ventilation, high pressure gas must be supplied to the airways of the patient on a constant basis. In this regard, a flow generator may be used with a conventional ventilator. Unfortunately, conventional ventilators typically operate at a lower pressure than the pressure required for CPAP therapy treatment.

Therefore, one design deficiency characterizing prior art flow generators is that such flow generators require the use of excessive supply pressure in order to create sufficient pressure at the patient. More particularly, it is understood that such prior art flow generators require up to 205 centimeters of $H_2O$ of supply pressure in order to create up to about 10 to 15 cm of $H_2O$ at the patient. However, federal standards limit the amount of supply pressure that can be utilized in CPAP therapy for certain patients. For example, in neonates, the recommended maximum supply pressure is limited to 120 centimeters (cm) of H2O. Furthermore, prior art flow generators require high supply pressure (e.g., 205 cm of H2O) in order to achieve a desired flow rate of 12 liters/minute (LPM) to the patient.

As may be appreciated, dangerously high supply pressures as required in prior art flow generators may subject the patient to the risk of injury. For example, high pressures within the patient airway can cause damage to lungs as well as other organs. In addition, exposure to high pressure in the patient airway may result in other respiratory complications. Another deficiency associated with prior art flow generators is that the requirement for excessive supply pressures requires a concomitant increased amount of power in order to generate the desired amount of patient pressure. In this regard, prior art flow generators are relatively inefficient and unsafe when used in CPAP therapy.

As can be seen, there exists a need in the art for a universal interface that may be adapted for providing continuous positive airway pressure (CPAP) with reduced supply gas pressure in order to minimize the risks posed by excessive pressures in the patient's airway. Furthermore, there exists a need in the art for a universal interface for CPAP ventilation that is configured to operate with a standard ventilator at a supply pressure of no greater than about 120 cm of H2O in order to provide up to about 15 cm of H2O at the patient, depending on the supply pressure.

In addition, there exists a need in the art for a universal interface for CPAP therapy that is configured to provide a flow rate of up to about 12 liters/minute to the patient while the supply pressure is limited to 120 cm of H2O. Also, there exists a need in the art for a universal interface for CPAP therapy that is of simple and thereby inexpensive design and which is specifically configured to sustain a positive airway pressure at the patient with minimal supply pressure while reducing exhalation resistance in order to improve the work of breathing.

BRIEF SUMMARY OF THE INVENTION

The present invention specifically addresses and alleviates the above referenced deficiencies associated with flow generators of the prior art. More particularly, the present invention is a universal interface that is adapted for providing continuous positive airway pressure (CPAP) with reduced supply gas pressure as compared to flow generators of the prior art. In this manner, the universal interface of the present invention minimizes risks posed by excessive pressure in the patient's airways.

More particularly, the universal interface of the present invention is specifically configured to operate with a standard ventilator at a maximum supply pressure of about 120 centimeters (cm) of $H_2O$ in order to deliver pressure to the patient of up to about 15 cm of $H_2O$ at a flow rate of up to about 12 liters/minute. Advantageously, the universal interface as presently constructed provides increased efficiency in that it operates with the reduced supply pressure while still providing a constant positive pressure within the patient's airways. Furthermore, the universal interface accomplishes the above with minimal pressure resistance during inhalation and exhalation phases of breathing at the patient.

Reduced operating pressure in the universal interface of the present invention is facilitated by including unique taper geometry within certain portions of the interface body. More specifically, the universal interface includes a pair of exhalation passageways and supply passageways which are each provided with a taper portion. The taper portion is specifically configured to minimize pressure resistance during inhalation and exhalation.

It should be noted that the universal interface may be configured for either non-invasive or invasive CPAP therapy. Implementing non-invasive CPAP therapy with the universal interface may be facilitated with the use of a nose piece member or a face mask such as mounted on a patient's head. Alternatively, the universal interface may be adapted for invasive CPAP therapy wherein a tracheal tube may be inserted into the patient to provide air to the patient's lungs.

If utilized, the nose piece member is preferably formed of a soft, elastic polymeric material that provides a comfortable surface against the patient's skin. Air is directed into the patient's nose through a pair of nostril engaging stems formed in the nose piece member that provide an efficient fluid path between the patient's nose and the universal interface. The nostril engaging stems include a peripheral wall having a D-shaped configuration to anatomically conform to the patient's nostrils.

The universal interface may include a pressure tube and a supply tube which extends from opposite sides thereof. The supply tube may be included with the universal interface to supply gas from a gas source to the patient during CPAP therapy. The pressure tube is included to provide a means by which pressure may be measured during breathing of the patient. A pressure fitting and a supply fitting may be included with the universal interface in order to facilitate mounting of the pressure tube and supply tube, respectively.

The interface body may be comprised of a spaced pair of generally parallel breathing passageways. A corresponding pair of supply passageways are also included with the universal interface and are fluidly connected to respective ones of the breathing passageways. The interface body may also have a spaced pair of exhalation passageways that are also fluidly connected to respective ones of the breathing passageways. The supply passageways may be generally coaxially aligned the breathing passageway to facilitate in-flow of supply gas. Each one of the breathing passageways is comprised of the patient passageway which terminates at a pair of patient ports to which the nostril engaging stems of the nose piece member connect. The exhalation passageways intersect the patient passageways to collectively form the breathing passageways. The patient passageways may intersect the exhalation passageways at an angle of from about 20° to about 60° although any angle may be utilized.

Each one of the supply passageways is configured to introduce pressurized gas into the patient passageways such as during the inspiration phase of the breathing cycle. A supply manifold may be integrally formed with the universal interface in order to supply pressure to the breathing passageways. The supply manifold may have the supply passageways extending therefrom which are configured to introduce pressurized gas to an interior of each of the supply passageways and, ultimately, into the patient passageways. Because the supply manifold is in fluid communication with the gas source via the supply tube, the supply manifold receives the pressurized gas therefrom and introduces the gas into the patient passageways via the pair of jet venturis. Notably, each one of the jet venturis include the tapered geometry for performance enhancement.

More particularly, the tapered portion of each one of the jet venturis tapers outwardly along a direction from the supply manifold toward the patient passageway. The taper angle of the taper portion is in the range from about 0.5° to about 10° and is preferably about 2.5°. The jet venturi may have a conical shape and, in this regard, the taper portion defines a minor diameter. It should also be noted that the supply passageways may be configured in a variety of cross-sectional shapes such as rectangular, oval, or a generally rounded shape.

If provided with a circular cross-sectional shape, at least at the minor diameter, then the taper portion of each one of the jet venturis preferably has a length that is in the range of from about 0.25 to about 3 times the minor diameter of the taper portion. A constant section portion may additionally be provided in at least one of the jet venturis along with the taper portion. If included, the constant section portion defines a length that is preferably in the range of from about 2.5 to about 2 times the minor diameter.

Each one of the exhalation passageways also preferably includes a taper portion that tapers outwardly along a direction from the patient passageway toward the exhalation port. The taper portion of each one of the exhalation passageways preferably has a taper angle which is in the range from about 0.5° to about 10° and which preferably is about 5°. The exhalation passageway may have a generally rectangular cross-sectional shape although other cross-sectional shapes may be used such as circular, oval, etc. The taper portion defines a minor width occurring at an intersection of the exhalation passageway with a corresponding one of the patient passageways.

The exhalation passageway taper portion preferably defines a length that is in the range of from about 0.25 to about 3 times the minor width of the exhalation passageway taper portion. A constant section portion may optionally be provided along with the taper portion in the exhalation passageways. If included, the constant section portion has a minor width that is preferably equivalent to that of the taper portion and has a length that is in the range of from about 0.25 to about 2 times the minor width.

Because of the unique geometry (i.e., tapered geometry) of the jet venturis and the exhalation passageways, exhaled air from the patient may be efficiently exhausted from the patient's mouth. In addition, air may be efficiently inhaled due to the provision of supply gas originating from the supply manifold and passing through the jet venturis. The universal interface may further include a pressure passageway which is provided for the purpose of measuring pressure at the patient airways. In this regard, pressure transducers may be placed in fluid communication with the pressure passageway such that pressure of the patient may be measured.

BRIEF DESCRIPTION OF THE DRAWINGS

These as well as other features of the present invention will become more apparent upon reference to the drawings wherein:

FIG. 6 is a side view of the interface body illustrating the relative orientations of the exhalation manifold and pressure manifold;

FIG. 7 is a front view of the interface body illustrating a well portion surrounding the pair of patient passageways and further illustrating a pressure passageway opening into the well portion and being located between the pair of patient passageways; and FIG. 8 is a partial cross-sectional top view of the interface body illustrating an L-shaped pressure passageway extending from the well portion of the interface body to a pressure port of the interface body.

DETAILED DESCRIPTION OF THE INVENTION

Figure 1:
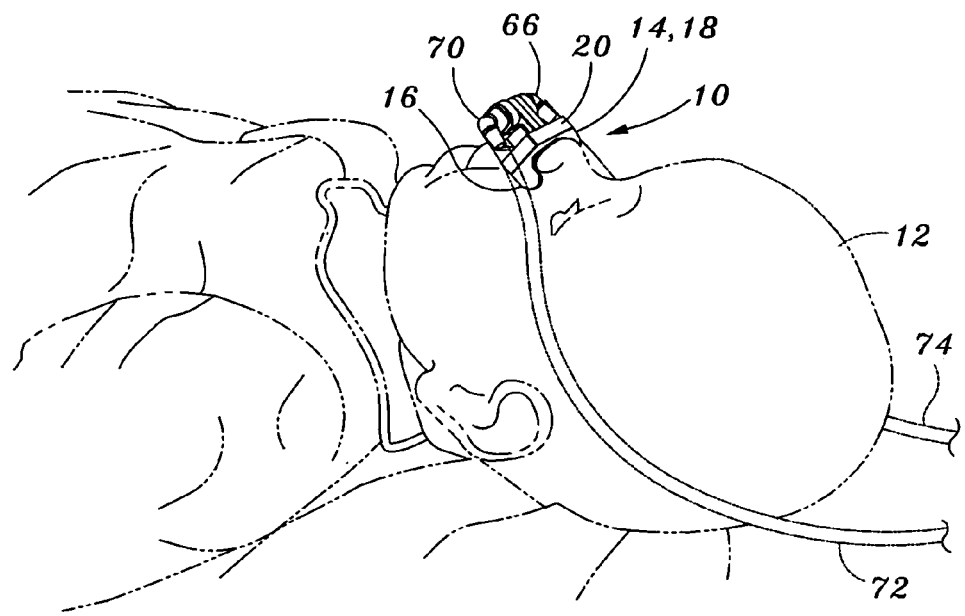
FIG. 1 is a perspective view of a universal interface of the present invention as utilized on a patient's face.

Referring now to the drawings wherein the showings are for purposes of illustrating preferred embodiments of the present invention only, and not for purposes of limiting the same, FIG. 1 perceptively illustrates the universal interface 20 as applied to an infant patient 12. The universal interface 20 includes a pressure tube 72 and a supply tube 74 attached on opposite sides of the universal interface 20 and extending around the patient's 12 head. As was mentioned above, the universal interface 20 of the present invention is specifically adapted to provide continuous positive airway pressure (CPAP) to the patient 12 at a reduced supply pressure when the universal interface 20 is used with a standard ventilator.

In particular, the universal interface 20 is specifically configured to operate at a pressure no greater than about 120 centimeters (cm) of $H_2O$ in order to deliver pressure to the patient of up to about 10 to 15 cm of $H_2O$ at a flow rate of up to about 12 liters/minute. In this regard, the universal interface 20 of the present invention provides increased efficiency in that it requires decreased supply pressure in order to provide a constant positive pressure within the patient's 12 airway. In addition, the universal interface 20 is specifically configured to minimize pressure resistance during inhalation and exhalation phases of breathing. The universal interface 20 facilitates this by reducing the required supply pressure of operation down to no greater than about 120 centimeters of $H_2O$.

The universal interface 20 accomplishes the reduced operating pressure by including a unique taper geometry within a pair of exhalation passageways 64 as well as in a corresponding pair of jet venturis 56 that interconnect a supply manifold 50 to a pair of patient passageways 38. The universal interface 20 may be configured for use in a non-invasive CPAP application such as using a mouth adapter or a nose piece member 16 as shown in FIG. 1. The nose piece member 16 may be mounted on the universal interface 20 and is preferably configured to anatomically conform to the patient's 12 nostrils 14 such as the nostrils 14 of the infant shown in FIG. 1.

The nose piece member 16 is preferably formed of an elastic polymeric material so as to provide a soft membrane between the universal interface 20 and the patient's 12 face. The nose piece member 16 preferably includes a pair of outwardly extending nostril engaging stems each having an axially extending aperture which is formed through the nose piece member 16. The nostril engaging stems allow for fluid communication to the patient passageways 38 of the universal interface 20. The nose piece member 16 is also preferably configured to be removably engaged to and retained within a well portion 28 of the universal interface 20 via frictional fit or via other means of securement such as adhesive or mechanical interconnection.

Preferably, the nostril engaging stems which outwardly protrude from the interface are provided with a peripheral wall having a D-shaped configuration to anatomically conform to the patient's 12 nostrils 14. In this regard, the nose piece member 16 that may be included with the present invention is similar to that shown and described in published U.S. Patent Application Publication No. 20030200970, filed Oct. 30, 2003 by Stenzler et al. and which is entitled, Infant Breathing Assist Apparatus, the entire contents of which is expressly incorporated by reference herein.

The universal interface 20 of the present invention is also preferably configured for use in invasive CPAP applications such as wherein a tracheal tube may be inserted into the patient. The tracheal tube may be used in conjunction with the universal interface 20 in applying CPAP therapy treatment. However, because infants are generally nose-breathers, it is contemplated that the universal interface 20 may be more commonly utilized in non-invasive CPAP therapy. In this regard, the nose piece member 16 or a mask interface may be disposed on the nose and/or mouth of the patient 12. Advantageously, regardless of whether the universal interface 20 is used in invasive or non-invasive CPAP applications, the interface is specifically configured to minimize pressure to no greater than about 120 centimeters of H2O in order to deliver pressure to the patient of up to about 10 to 15 cm of $H_2O$.

As can be seen in FIG. 1, the universal interface 20 may be mounted on the patient 12 and may have the pressure tube 72 extending from one side of the universal interface 20. The supply tube 74 may extend from an opposite side of the universal interface 20. The supply tube 74 is configured to supply gas from a gas source 76 to the patient 12 during CPAP therapy. The pressure tube 72 is provided to allow for a means of measuring pressure during breathing at the patient 12. Such pressure measurement may be facilitated using a pressure transducer or other pressure measurement instruments.

Figure 2:
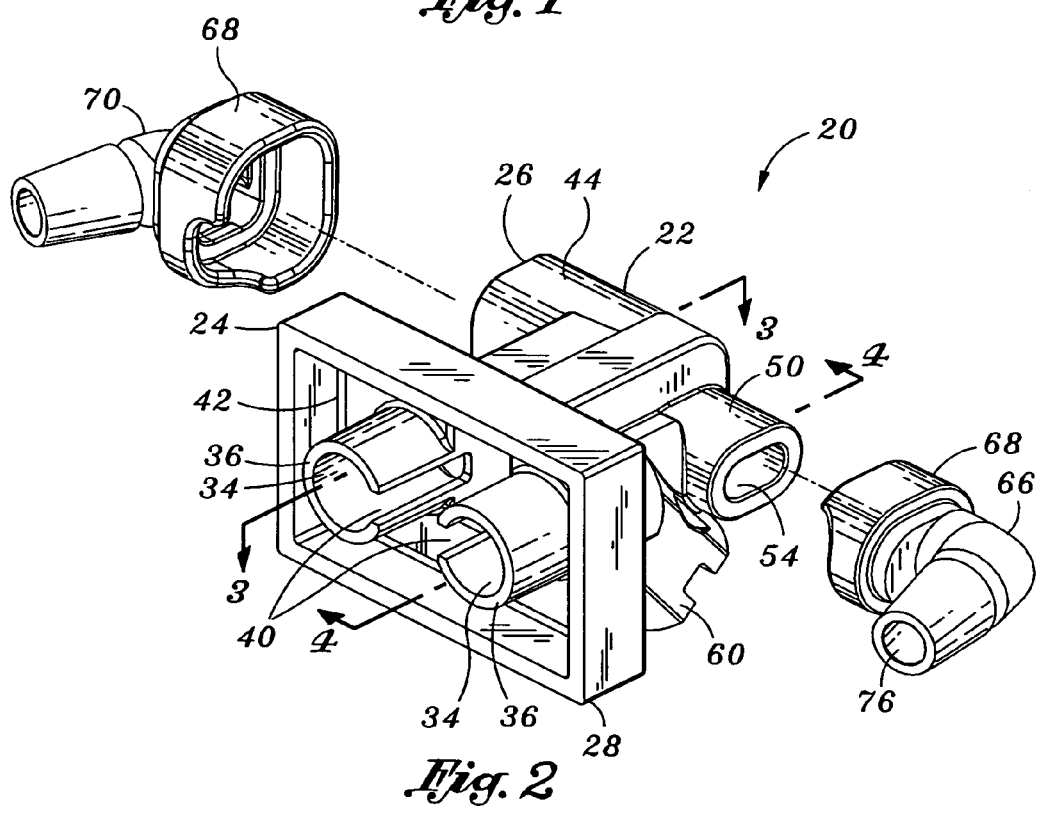
FIG. 2 is an exploded perspective view of the universal interface as worn by the patient shown in FIG. 1 and illustrating an interface body having a supply fitting and a pressure fitting attachable to the interface body and having supply and pressure tubes extending, respectively, therefrom along the patient's head.
Figure 3:
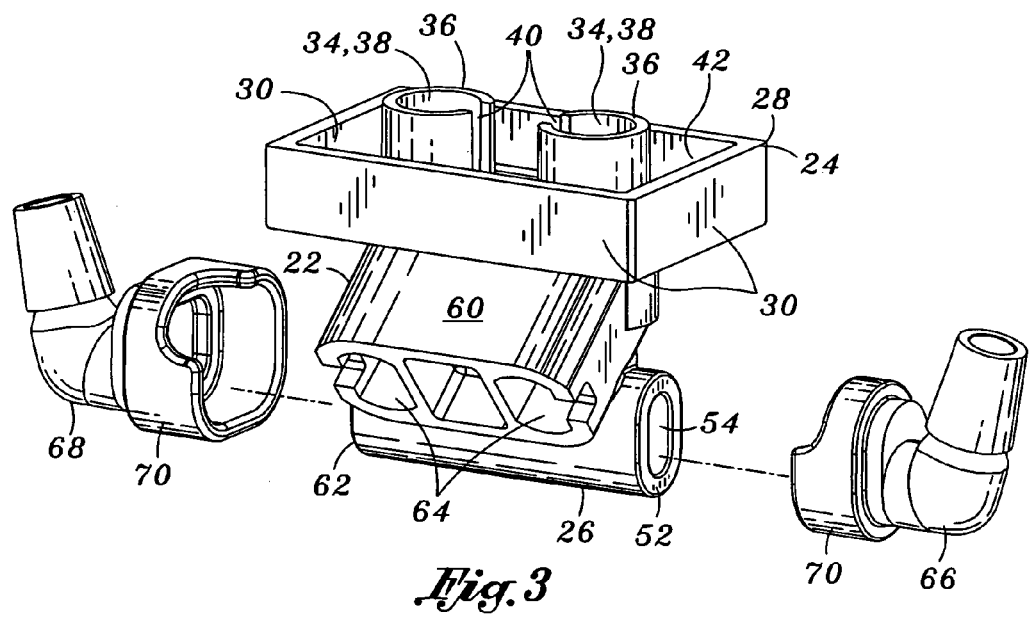
FIG. 3 is a perspective view of the universal interface in an orientation illustrating an exhalation manifold that is integrally formed into the interface body.

Referring now to FIG. 2, shown is the universal interface 20 in a perspective view wherein the universal interface 20 includes an interface body 22. FIG. 2 also illustrates a supply fitting 66 and a pressure fitting 70 disposed on opposite sides of the interface body 22. As was earlier mentioned, the pressure tube 72 may be interconnected to the interface body 22 using the pressure fitting 70 while the supply tube 74 may be interconnected to the interface body 22 using the supply fitting 66. Flanges 68 may be provided on the supply fitting 66 as well as on the pressure fitting 70 in order to facilitate interconnection thereof to the interface body 22.

Ideally, the interface body 22 is sized and configured complementary to the flanges 68 of the supply and pressure fittings 66, 70 to facilitate mounting thereupon. In this regard, the supply and pressure fittings 66, 70 may be connected to the interface body 22 using a variety of means including, but not limited to, sonic welding, adhesive and frictional fit. Advantageously, assembly and manufacturer of the universal interface 20 is facilitated by providing the supply and pressure fittings 66, 70 as separate components from the interface body 22.

Figure 5:
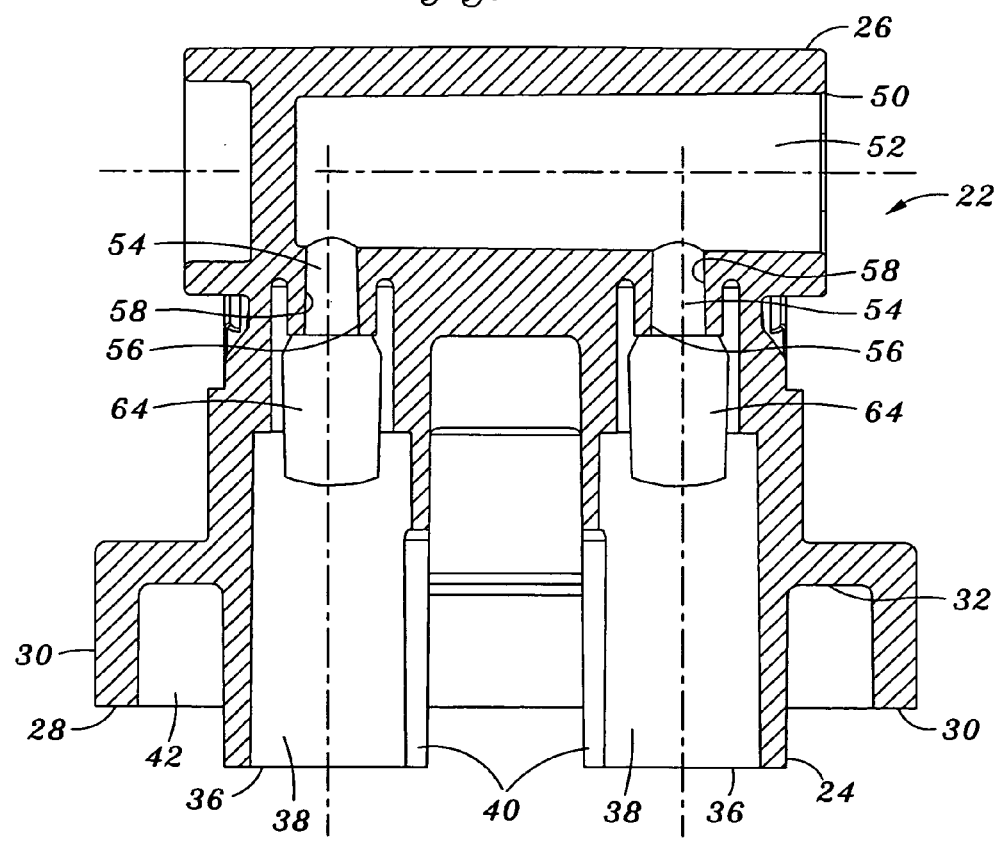
FIG. 5 is a top cross-sectional view of the interface of FIG. 2 and illustrating a supply passageway having a pair of the jet venturis extending therefrom and being coaxially aligned with the patient passageways.

Referring to FIGS. 2 and 5, shown is the interface body 22 which, in its broadest sense, may be comprised of a spaced pair of breathing passageways 34 having a corresponding pair of the supply passageways 54 fluidly connected thereto and having the pair of exhalation passageways 64 fluidly connected to the breathing passageways 34. As can be seen, the pair of supply passageways 54 may be generally aligned with the breathing passageways 34. For example, the supply passageways 54 may be coaxial with the breathing passageways 34. Each one of the breathing passageways 34 is comprised of a patient passageway 38 that terminates at a patient port 36 near a proximal end of the universal interface 20.

Figure 4A:
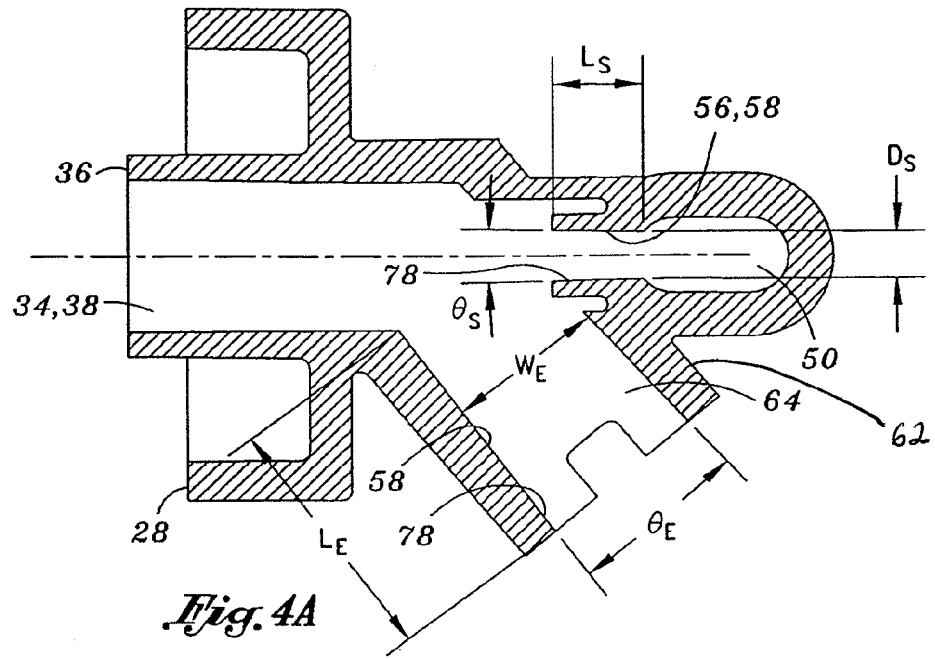
FIG. 4a is a cross-sectional view taken along line 4-4 of FIG. 2 and illustrating an exhalation passageway and a jet venturi each having tapered portions which are specifically configured to minimize supply pressure and reduce exhalation resistance, respectively.
Figure 4B:
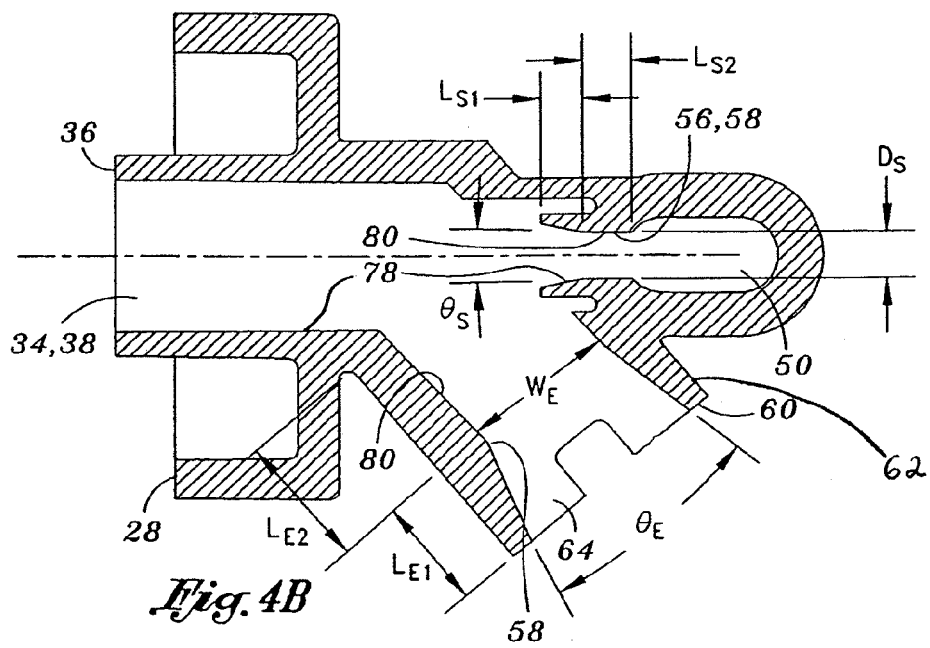
FIG. 4b is a cross-sectional view of the interface body taken along line 4-4 and illustrating the exhalation passageway and jet venturi having a constant section portion in addition to the taper portion.

The patient passageway 38 is preferably adapted to supply gas to the patient 12. The exhalation passageways 64 are preferably adapted to expel gas from the patient 12 during the expiration phase of the breathing cycle. The exhalation passageways 64 preferably intersect the patient passageways 38 to form the breathing passageways 34. As can be seen in FIG. 4a and 4b, the patient passageway 38 may intersect the exhalation passageway 64 at an angle from about 20° to about 60° although it is contemplated that the patient 38 and exhalation passageways 64 may intersect one another at any suitable angle.

As was earlier mentioned, in order to enhance performance of the universal interface 20 during CPAP therapy, each one of the supply passageways 54 is preferably axially aligned with a corresponding one of the patient passageways 38. Each one of the supply passageways 54 is also preferably configured to introduce pressurized gas into the patient passageways 38 such as during the inspiration phase of the breathing cycle. In this regard, the patient passageways 38 and exhalation passageways 64 are preferably configured to provide reduced operating pressure, namely, limiting supply pressure to no greater than about 120 cm of $H_2O$.

As is shown in the figures, the interface body 22 has the proximal end 24 (disposed near the patient ports 36) and a distal end 26 (disposed near the supply and pressure ports 46, 52). As best shown in FIG. 5, extending between the proximal and distal ends 24, 26 are the patient passageways 38 which are interconnected to the supply manifold 50 by the corresponding pair of supply passageways 54. The patient passageways 38 are preferably disposed in parallel relationship to each other. The supply manifold 50 has the supply passageways 54 extending laterally outwardly therefrom. The supply passageways 54 interconnect the corresponding pair of patient passageways 38 to the supply manifold 50, as is shown in FIG. 5.

In this regard, the interface body 22 includes the supply manifold 50 having the supply passageways 54 extending therefrom for the purpose of introducing pressurized gas to the interior of each of the supply passageways 54 and, ultimately, into the patient passageways 38. As was earlier mentioned, pressurized gas may be supplied to the interface body 22 via the supply tube 74 which draws pressurized gas from the gas source 76. The supply manifold 50 splits fluid flow from the supply tube 74 into each of the patient passageways 38.

Because the supply manifold 50 is in fluid communication with the gas source 76 by the supply tube 74, it is able to receive the pressurized gas therefrom and introduce the gas into the patient passageways 38 via the pair of jet venturis 56. Advantageously, the pair of jet venturis 56 each have a tapered geometry for performance enhancement. As can be seen in FIGS. 2-4b, the supply manifold 50 may be configured with a generally oval cross-sectional shape although the supply manifold 50 may be provided in any size and configuration including alternative cross-sectional shapes such as circular shapes and rectangular shapes or combinations thereof.

At the proximal end 24 of the interface body 22, a well portion 28 is provided and through which the pair of patient ports 36 protrude. The patient ports 36 are shown as being generally cylindrically-shaped hollow tubular members. The well portion 28 may be generally configured as a rectangularly-shaped, open, box-like structure collectively formed by a set of well sidewalls 30 and a well basewall 32 which forms a bottom of the well portion 28. The patient ports 36 may be configured to generally extend outwardly past an upper edge of the well sidewalls 30 as shown in the figures. In this regard, the well portions 28 may be specifically adapted to allow for fitment of the nose piece member 16 therewithin. Each one of the patient ports 36 may include a slot 40 formed on an inner-side thereof. The slots 40 may facilitate pressure measurement at the patient 12 via the pressure manifold 44 in a manner that will be described in greater detail below.

Referring to FIG. 6-8, shown is the interface body 22 having the pressure manifold 44 integrally formed therewith. As can be seen, the pressure manifold 44 includes an exhalation port 62 having a generally rectangular shape which is sized and configured to be compatible to the pressure fitting 70. As was earlier mentioned, the pressure passageway 48 is provided to allow for pressure measurement at the patient 12 during CPAP therapy treatment. As can be seen in FIG. 8, the pressure passageway 48 may extend from the pressure port 46 to a well opening 42 formed in the well basewall 32 although the pressure passageway may be configured as a straight passageway or any alternative shape.

As best seen in FIG. 7, the well opening 42 is disposed slightly above and generally between the pair of patient passageways 38. The open nature of the patient ports 36 allows for pressure measurements at the patient 12 due to the opposing pair of slots 40. Although the pressure passageway 48 is shown as being generally L-shaped in a top view and as having a generally rectangular cross-section, it is contemplated that the pressure port 46 may be formed in any configuration including having a generally linear arrangement wherein the pressure passageway 48 extends in a straight line from the well opening 42 at the proximal end 24 of the interface body 22 toward the pressure port 46 at the distal end 26 of the interface body 22.

However, in order to provide comfortable wearing of the universal interface 20 by the patient 12, it is contemplated that the pressure port 46 is generally on a side opposite that of the location of the supply port 52 and that the pressure and supply tubes 72, 74 may extend around the patient's 12 head on opposite sides thereof. Furthermore, although the pressure passageway 48 is shown as having a generally rectangularly shape cross-section as can be seen in FIG. 7, it is contemplated that the pressure passageway 48 may alternatively be provided in a variety of shapes and sizes including a circular and/or oval cross-sectional shape.

Referring still to FIGS. 2-6, shown is the interface body 22 having the exhalation manifold 60 integrally formed therewith. As best seen in FIGS. 4-a and 4-b, the exhalation manifold 60 intersects the patient passageways 38 at an angle. Advantageously, the exhalation manifold 60 includes the exhalation passageways 64 extending from the exhalation port 62 and intersecting the patient passageways 38.

During the expiration phase of breathing, the larger cross-sectional area of the exhalation passageways 64 relative to the cross-sectional area of the supply passageways 54 allows for the efficient exhalation of expiratory air. Advantageously, the various functional portions of the interface body 22 (i.e., pressure manifold 44, supply manifold 50, exhalation manifold 60, breathing passageways 34) are preferably, but optionally, integrally formed in the interface body 22 in order to facilitate assembly and manufacture thereof. Furthermore, the relative sizes and shapes of the breathing passageway 34, patient passageway 38, pressure passageway 48, supply passageway 54 and exhalation passageways 64 facilitates reduced pressure resistance against flow and, depending on the supply gas pressure, can be configured to generate the desired flow rate.

Importantly, each one of the supply passageways 54 includes the jet venturi 56 which is specifically configured to have a taper portion 78 formed along an inner wall 58 thereof. The taper portion 78 tapers outwardly along a direction from the supply manifold 50 toward the patient passageway 38 in order to facilitate the inspiration phase of the CPAP therapy. It is contemplated that the taper angle $\theta_S$ of the taper portion 78 is provided in the range from about 0.5° to about 10° and is preferably about 2.5°. In this manner, the requirement of the supply gas pressure is reduced while still providing the required patient 12 pressure as compared to the supply gas pressure required for producing the patient 12 pressure in conventional flow generators.

In the interface body 22 of the present invention, it should be noted that the relationship of the cross-sectional area of the supply passageways 54 is critical with respect to the degree of taper in the jet venturi 56. For example, as can be seen in FIGS. 4a and 4b, the jet venturi 56 taper portion 78 defines a minor diameter characterized by the symbol $D_S$. It has been discovered during performance testing that an optimal length $L_{S1}$ of the taper portion 78 of the jet venturi 56 is in the range of from about 0.25 to about 3 times the minor diameter $D_S$ of the taper portion 78.

As can be seen in FIG. 4a, the minor diameter $D_S$ of the jet venturi 56 occurs at a junction of the supply passageway 54 (i.e., jet venturi 56) with the supply manifold 50 which is the main passageway for the supply gas. Alternatively, depending on the desired CPAP pressure, the jet venturi 56 may be provided with a constant section portion 80 which is preferably interposed between the taper portion 78 of the jet venturi 56 and the supply manifold 50. As shown in FIG. 4b, the minor diameter $D_S$ of the jet venturi 56 is generally equivalent to that of the constant section portion 80 minor diameter. For configurations including the constant section portion 80 in the jet venturi 56, it is contemplated that the constant section portion 80 defines a length $L_{S2}$ that is in the range of from about 2.5 to about 2 times the minor diameter $D_S$.

Referring now to FIGS. 4a with respect to the exhalation passageways 64, each preferably also includes a taper portion 78 which tapers outwardly along a direction from the patient passageway 38 toward the exhalation port 62. The taper portion 78 of each one of the exhalation passageways 64 defines a taper angle $\theta_E$ which is in the range of from about 0.5° to about 10° and which preferably is about 5°. A geometric relationship between the cross-sectional area and shape of the exhalation passageways 64 is also provided in a manner similar to that described above with respect to the jet venturi 56.

In this regard, the exhalation passageway 64 taper portion 78 defines a minor width $W_E$ at an intersection with the patient passageway 38. The exhalation passageway 64 taper portion 78 defines a length $L_{E1}$ that is in the range of from about 0.25 to about 3 times the minor width $W_E$ of the exhalation passageway 64 taper portion 78. As was earlier mentioned, the inclusion of the taper geometry in the exhalation passageways 64 provides for less exhalation resistance for easier breathing during CPAP therapy.

Similar to that described above for the jet venturi 56, a constant section portion 80 may also be provided along with a taper portion 78 for the exhalation passageways 64. The constant section portion 80 is shown in FIG. 4a and is interposed between the patient passageways 38 and the taper portion 78. The minor width $W_E$ of the taper portion 78 is preferably equivalent to that of the constant section portion 80. The preferred geometric relationship between the minor width $W_E$ and a length $L_{E2}$ of the constant section portion 80 is such that the length $L_2$ is in the range of from about 0.25 to about 2 times the minor width $W_E$.

Because of the unique geometries in the interface body 22 including the geometry of the taper portion 78 (and optionally, of the constant section portion 80) of the exhalation passageways 64, exhaled air originating from the patient's 12 lungs may be efficiently exhausted. It is contemplated that various devices may be connected to the interface body 22 at the exhalation ports 62 to facilitate operation of the universal interface 20 although the exhalation ports 62 may optionally remain open to the free atmosphere.

Regarding materials from which the universal interface 20 may be fabricated, it is contemplated that a substantially rigid polymeric material may be utilized for the interface body 22. Likewise, the pressure and supply fittings 70, 66 are preferably fabricated from a similar or at least compatible material. In this regard, the interface body 22 is preferably, but optionally, molded such as by injection molding. It is contemplated that the polymeric material may include Lexan or other acrylic-type materials which are preferably FDA approved. However, it is contemplated that the interface body 22 and pressure and supply fittings 70, 66 may be fabricated using any suitable material.

The operation of the universal interface 20 will now be described in reference to the figures. The universal interface 20 may be provided with the nose piece member 16 which may be sized and configured to frictionally fit within the wall portion thereof. After mounting of the nose piece member 16, the universal interface 20 may then be mounted upon the patient's 12 head. Both the pressure and supply tubes 72, 74 may then be connected to respective ones of the pressure and supply fittings 70, 66 at the interface body 22. The source or pressurized gas may be supplied via the pressure tube 72 into the supply manifold 50. Pressure transducers may be placed in fluid communication with the pressure tube 72 such that pressure of the patient 12 may be measured during operation of the universal interface 20.

Once the universal interface 20 is mounted to the patient 12 and pressurized gas is supplied thereto via the supply tube 74, pressure is then supplied to the patient's 12 airway which is preferably above atmospheric pressure in order to facilitate spontaneous breathing in the patient 12. More particularly, patient pressure delivered to the patient is preferably up to about 15 cm of $H_2O$. During the inspiration phase, the patient 12 draws in air at the patient passageways 38 which is directly connected to corresponding ones of the supply passageways 54. Supply pressure of up to about 120 cm of $H_2O$ is provided through the supply manifold 50 to the supply passageways 54 (i.e., jet venturis 56). Due to the unique taper geometry of the jet venturis 56, breathing gas and/or atmospheric air may be sucked in from the pair of exhalation passageways 64 assisted by the supply gas from the supply passageways 54. Minimal supply pressure is required to provide the same amount of patient 12 pressure at the patient port 36 compared to the pressure required to operate a conventional interface. During the inspiratory flow, intake of breathing gas and/or atmospheric air through the exhalation passageways 64 is thereby assisted by supply gas through the supply passageways 54 which counteracts the tendency of pressure to lower during the inspiratory phase.

During the expiratory phase, air that is to be exhausted from the patient's 12 lungs is directed through the pair of patient passageways 38 and out of the exhalation passageways 64. Because of the unique configuration of the taper portion 78 provided in each one of the exhalation passageways 64, the interface body 22 provides less exhalation resistance at the exhalation passageways 64. In this manner, the exhalation passageways 64 in conjunction with the jet venturis 56 of the supply passageways 54 provide for better work of breathing with reduced supply pressure and less overall power in order to provide the desired amount of pressure at the patient 12. In this regard, the universal interface 20 of the present invention provides a device which can be used with conventional flow generators and which becomes more efficient and safe to operate in regard to the risk of overpressure at the patient 12.

Additional modifications and improvements of the present invention may also be apparent to those of ordinary skill in the art. Thus, the particular combination of parts as described and illustrated herein is intended to represent only certain embodiments of the present invention and is not intended to serve as limitation of alternative devices within the spirit and scope of the invention.

What is claimed is:

1. A universal interface, comprising:
   an interface body having a spaced pair of breathing passageways extending therethrough with a corresponding pair of supply passageways fluidly connected thereto;
   wherein;
   each one of the breathing passageways is comprised of a patient passageway adapted to supply gas to the patient and intersecting an exhalation passageway adapted to expel gas from the patient;
   each of the patient passageways terminating in a cylindrically shaped hollow tubular patient port;
   a well opening disposed between said patient ports;
   opposing slots defined within said patient ports and configured to fluidly couple said patient ports with said well opening while said universal interface is coupled with patient;
   a pressure manifold opening into said well opening and configured to allow pressure measurement at the patient;
   each one of the supply passageways being axially aligned with a corresponding one of the patient passageways and being configured to introduce pressurized gas thereinto; and
   each one of the supply passageways forming a jet venturi having a taper portion tapering outwardly toward the patient passageway.

2. The universal interface of claim 1, wherein the patient and exhalation passageways intersect one another at an angle of about 20° to about 60°.

3. The universal interface of claim 1, wherein a taper angle of the taper portion is in the range of 0.5° to about 10°.

4. The universal interface of claim 3, wherein the taper angle of the jet venturi taper portion is about 2.5°.

5. The universal interface of claim 1, wherein:
   the jet venturi taper portion defines a minor diameter at the junction of the supply passageway and supply manifold; and
   the jet venturi portion defining a length thereof that is in the range of from about 0.25 to about 3 times the minor diameter.

6. The universal interface of claim 5, wherein the jet venturi further includes a constant section portion interposed between the taper portion and the supply portion.

7. The universal interface of claim 6 wherein:
   the minor diameter is generally equivalent to that of the constant section portion; and
   the constant section portion defining a length thereof that is in the range of from about 0.25 to about 2 times the minor diameter.

8. The universal interface of claim 1, wherein each one of the exhalation passageways includes a taper portion tapering outwardly along a direction from the patient passageway toward the exhalation passageway.

9. The universal interface of claim 8, wherein a taper angle of the taper portion is in the range of from about 0.5° to about 10°.

10. The universal interface of claim 9, wherein the taper angle of the exhalation passageway taper portion is about 5.

11. The universal interface of claim 8, wherein:
    the exhalation passageway taper portion defines a minor width at an intersection with the patient passageway; and
    the exhalation passageway taper portion defining a length thereof that is in the range of from 0.25 to about 3 times the minor width.

12. The universal interface of claim 11, wherein each one of the exhalation passageways further includes a constant section portion interposed between the patient passageway and the taper portion.

13. The universal interface of claim 12, wherein:
    the minor width is generally equivalent to that of the constant section portion; and
    the constant section portion defining a length thereof that is in the range of from about 0.25 to about 2 times the minor width.

14. The universal interface of claim 1, further comprising a supply fitting and a pressure fitting disposed on free ends of a supply manifold and pressure manifold, respectively,
    wherein the supply manifold has the supply passageways extending laterally therefrom.

* * * * *

UNITED STATES PATENT AND TRADEMARK OFFICE
CERTIFICATE OF CORRECTION

| | | |
|---|---|---|
| PATENT NO. | : 8,100,125 B2 | Page 1 of 1 |
| APPLICATION NO. | : 11/241303 | |
| DATED | : January 24, 2012 | |
| INVENTOR(S) | : Steven Duquette et al. | |

It is certified that error appears in the above-identified patent and that said Letters Patent is hereby corrected as shown below:

Col. 11, Claim 1, Line 23-24: Delete: "opening while said universal interface is coupled with patient;"

Insert: --opening while said universal interface is coupled with a patient;--

Signed and Sealed this

Fourth Day of September, 2012

David J. Kappos
*Director of the United States Patent and Trademark Office*